(12) United States Patent
Steger

(10) Patent No.: US 10,265,145 B2
(45) Date of Patent: Apr. 23, 2019

(54) BLANK FOR THE PRODUCTION OF A TOOTH PROSTHESIS

(71) Applicant: Heinrich Steger, Bruneck (IT)

(72) Inventor: Heinrich Steger, Bruneck (IT)

( * ) Notice: Subject to any disclaimer, the term of this patent is extended or adjusted under 35 U.S.C. 154(b) by 526 days.

(21) Appl. No.: 15/008,963

(22) Filed: Jan. 28, 2016

(65) Prior Publication Data

US 2016/0220337 A1 Aug. 4, 2016

(51) Int. Cl.
*A61C 13/00* (2006.01)

(52) U.S. Cl.
CPC ................................. *A61C 13/0022* (2013.01)

(58) Field of Classification Search
CPC .................................................. A61C 13/0022
See application file for complete search history.

(56) References Cited

U.S. PATENT DOCUMENTS

| 4,970,032 | A | 11/1990 | Rotsaert |
| 6,379,593 | B1 | 4/2002 | Datzmann et al. |
| 2011/0104643 | A1 | 5/2011 | Giordano |
| 2011/0189636 | A1 | 8/2011 | Thiel et al. |
| 2013/0224454 | A1 | 8/2013 | Jung et al. |
| 2014/0255875 | A1 | 9/2014 | Saliger |
| 2014/0377718 | A1 | 12/2014 | Korten et al. |

FOREIGN PATENT DOCUMENTS

| DE | 197 14 178 | 10/1998 |
| DE | 10 2009 019 447 | 11/2010 |
| DE | 20 2009 018 724 | 1/2013 |
| DE | 10 2011 055 393 | 5/2013 |
| DE | 10 2013 203 750 | 9/2014 |
| WO | 02/09612 | 2/2002 |
| WO | 2008/083358 | 7/2008 |
| WO | 2013/122662 | 8/2013 |

OTHER PUBLICATIONS

Austrian Search Report issued Jun. 30, 2015 in corresponding Austrian Patent Application No. 38/2015 (with English translation).

*Primary Examiner* — John E Uselding
(74) *Attorney, Agent, or Firm* — Wenderoth, Lind & Ponack, L.L.P.

(57) ABSTRACT

A blank, in particular a dental blank, for the production of a tooth prosthesis, includes a bed of a first material, and at least one core region which is embedded in the bed and which has a different color from the bed and includes a second material. The core region has a surface directed in the direction of the bed, and a boundary layer delimiting the bed relative to the surface of the core region is directed in the direction of the bed. The boundary layer simulates a dentine boundary between a dental enamel and a dentine, and the blank has at least two separate core regions with separate surfaces directed in the direction of the bed.

19 Claims, 5 Drawing Sheets

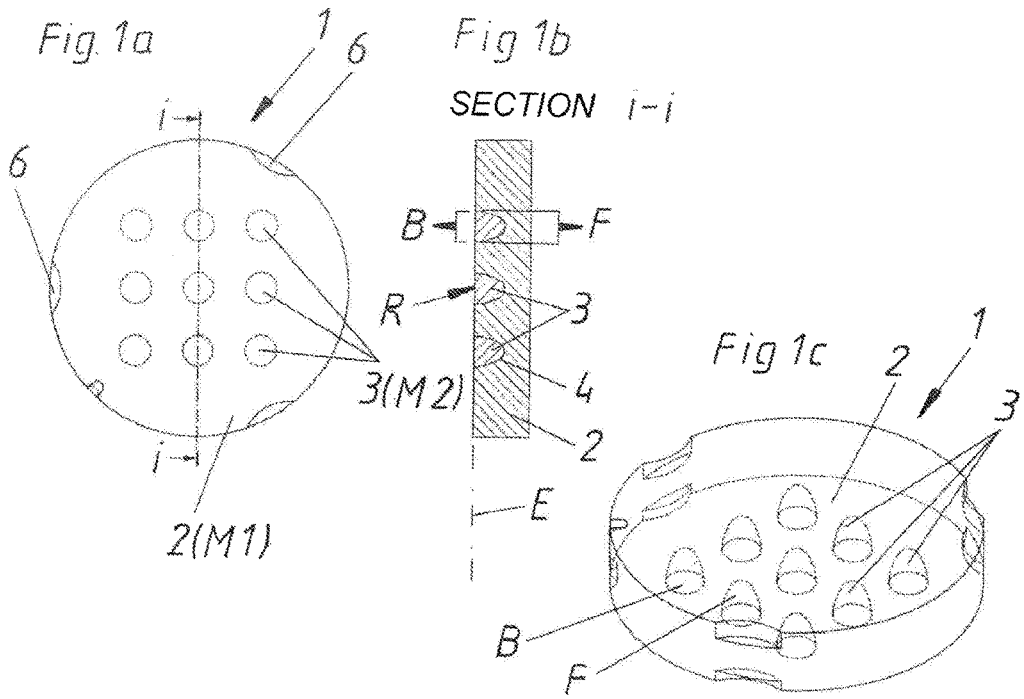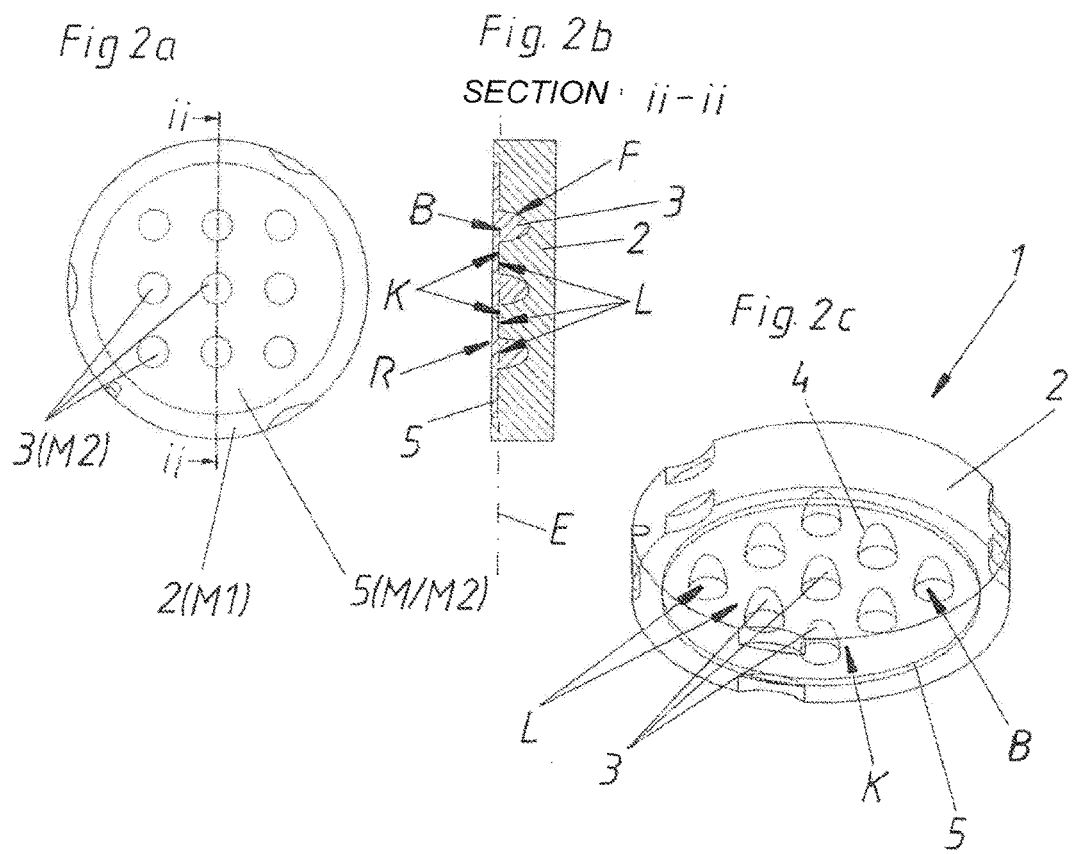

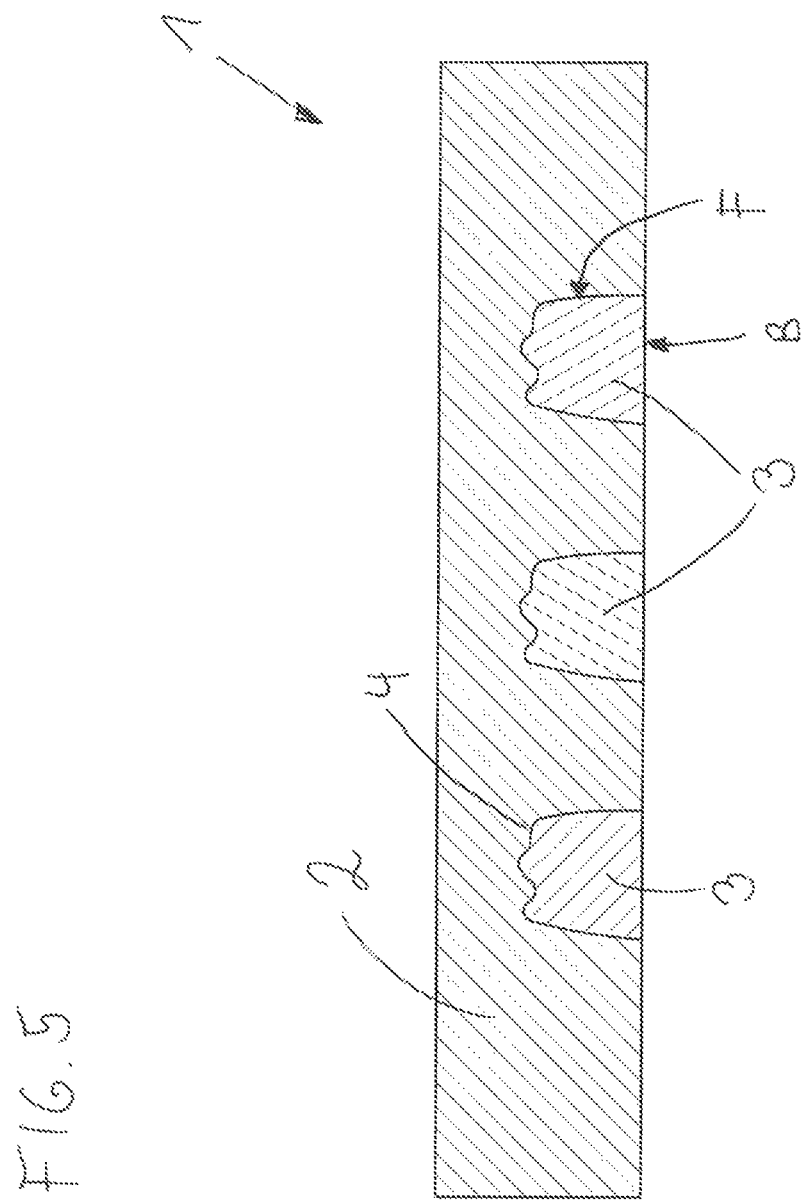

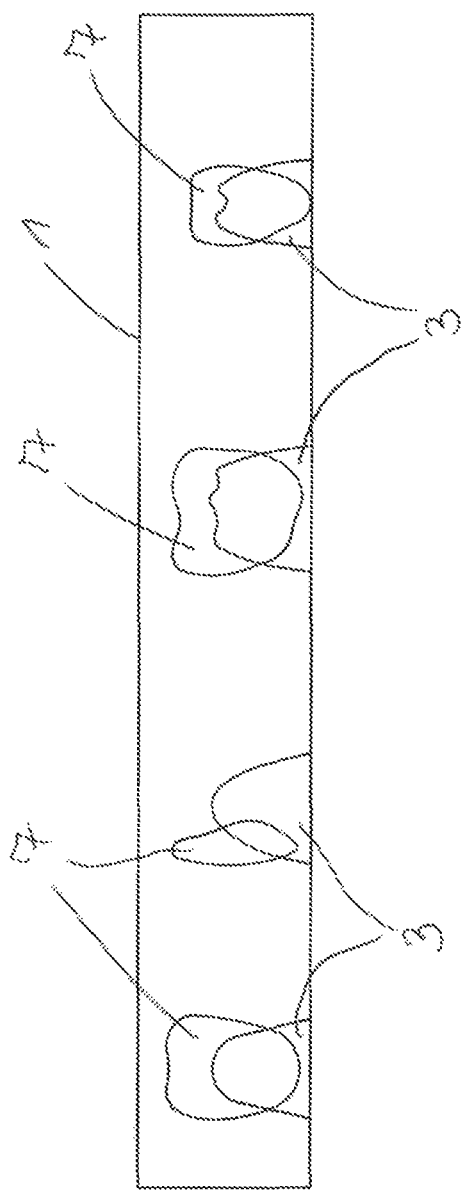

BLANK FOR THE PRODUCTION OF A TOOTH PROSTHESIS

BACKGROUND OF THE INVENTION

The invention concerns a blank, in particular a dental blank, for the production of a tooth prosthesis. The blank comprises a bed of a first material, and at least one core region which is embedded in the bed and which has a different color from the bed and comprises a second material. The core region has a surface directed in the direction of the bed.

Blanks for the production of a tooth prosthesis, which are made from various materials (for example various plastics) have already been known for some time.

There are, for example, cylindrical disks which in the axial direction comprise various layers of graduated shaded colors. In that way, it is possible to achieve a more natural color variation in dental restoration procedures.

An example of such a variant is disclosed in DE 10 2011 055 393 A1. That specification discloses the manufacture of a blank for artificial teeth, wherein the blank has a homogeneous color transition and the artificial teeth produced from the blank come close to the appearance of natural teeth. There are no visible separation lines at which it is possible to see the color transition between two materials which are of different colors. It is admittedly possible for the various profiles or structures of the plastic layers to be uniformly or non-uniformly distributed, to be of a wave-shaped, pyramid-shaped, cylindrical or cuboidal configuration, in which case however those structures which are important for manufacture can no longer be seen at all or can scarcely be seen in the finished blank due to the homogeneous color transition.

In a similar fashion, German patent DE 197 14 178 C2 describes a process for the production of a multi-colored shaped body for further processing to constitute tooth restoration, wherein there is a continuous color gradient as an essential feature.

In comparison, the invention further concerns a blank having a boundary layer delimiting the bed relative to a surface of the core region, that is directed in the direction of the bed. The boundary layer simulates a dentine boundary between a tooth enamel and a dentine. More specifically, in that case, the color graduation simulating the dentine core or the dentine boundary is produced in a certain approximation to reality from the point of view of shape.

An example of such a blank with an intentionally produced, relatively sharp dentine boundary is the so-called Vitablocs which are available on the market. They are generally of a size corresponding to a tooth so that an individual tooth or a dental prosthesis can be produced from that block.

U.S. Pat. No. 4,970,032 is known from the state of the art, describing multi-colored dental blanks, wherein individual teeth which have different color graduations are also produced.

A further specification disclosing a multi-colored dental blank is WO 2008/083358 A1. What is essential therein is that the different colored zones are arranged concentrically.

A further protection right with a shapeable blank involving different colors is WO 02/09612 A1.

DE 10 2013 203 750 A1 discloses a process for the production of a tooth prosthesis. This involves the preparation of reference data of optical properties of different dentine materials and translucent enamel materials of the tooth prosthesis. Target values are ascertained therefrom, in accordance with which a dental prosthesis shaped block having the desired boundary surface is selected and prepared by means of material removal.

DE 20 2009 018 724 U1 describes a shaped body comprising a material which is stabilized in respect of shape, and a process for the production thereof. This quite generally involves a second component being of a different pigmentation from the first component and the second component being arranged in the first component, with the formation of an interface, in such a way that the interface represents a spatially curved surface (for example a parabolic boundary line). The interfaces of the enamel-dentine boundary layers of the upper jaw and lower jaw teeth are assembled by means of a graphic software and the interface shape is generated in that way. That is very complicated and expensive and in practice has to be separately established and produced for each individual blank.

A disadvantage with the processes known from the state of the art is the relatively high level of complication and expenditure, in particular if a plurality of parts of a denture set or a plurality of teeth are to be produced.

SUMMARY OF THE INVENTION

The object of the present invention is therefore to provide a blank which is improved over the state of the art. In particular the invention seeks to provide that this blank simplifies the production of a tooth prosthesis and makes it faster.

Therefore, according to the invention, the blank has at least two separate core regions with separate surfaces directed in the direction of the bed. In that way, it is possible for a plurality of teeth which each have a visible dentine boundary also to be produced from a single blank in a simple fashion. Because the core regions and the surfaces directed in the direction of the bed are provided separately and thus spaced relative to each other, a plurality of teeth can be produced from one and the same blank, together with the core region simulating the dentine core and together with the bed simulating the tooth enamel. It is preferably provided that, in addition to the surface directed in the direction of the bed, each core region has a base surface adjoining the surface directed in the direction of the bed and facing away from the bed. In that respect, preferably each base surface lies in a base plane. More specifically, the base surfaces of all core regions are arranged in mutually spaced relationship in the blank. Thus, those base surfaces do not contact each other. In principle, the situation should admittedly not be excluded that a good many of the base surfaces are in contact with each other slightly or at least region-wise, but preferably the large part of those base surfaces, preferably all base surfaces, are not in contact with each other at all in a blank and are thus each produced separately from each other.

To achieve a shape which is as natural as possible for the dentine boundary, preferably the surface of the core region, that is directed in the direction of the bed, is substantially convex.

There are in principle two different embodiments for production of the blank. The first embodiment provides that the base surfaces also form an outside surface of the blank. This means that the individual core regions or the base surfaces of those core regions are to be seen at one side of the surface of the blank, by virtue of the differing coloration, as there they also form the surface.

In accordance with the alternative second embodiment, however, adjoining the base surfaces of the core regions is a basic layer which is oriented parallel to the base surfaces and which comprises a material different from the first material. In principle, the core region and the basic layer can also comprise mutually different materials. That simplifies in particular manufacture as the material of the core region can be cast into openings already prefabricated in the previously injection-molded bed. Preferably in that respect, the second material forms the material different from the first material, wherein the core regions are in one piece with the basic layer. The basic layer thus forms a kind of cover for the core regions which are embedded in the bed. In other words, it can thus be said that the surface of the basic layer, that is directed in direction of the bed, adjoins the base surfaces of the core regions and a contact surface of the bed, that is disposed in the base plane.

It is possible in principle for the blank to comprise three or more different materials. For simplicity of production, however, it is preferably provided that the blank only comprises the first material and the second material.

For simulation of the dentine boundary between a tooth enamel and a dentine or dentine core it is necessary for the materials used to be of differing colors. That differing coloration can be achieved by various methods. Particularly preferably for that purpose it is provided that the first material and the second material have mutually differing pigmentation and/or are of chemically differing nature and/or are of a mutually different density. The nature of the differing coloration can be decided upon in accordance with the respective situation of use.

The dentine boundary of a tooth prosthesis to be produced from a blank can be clearly seen with the eye in particular when the boundary layer extends within a range of a thickness of less than 0.3 mm, in particular a thickness of between 0.001 and 0.2 mm. The thickness can therefore vary within that range, in particular in dependence on the materials used. In other words, the more the core region is visible through the bed (therefore the "more transparent" the material of the bed is), the correspondingly less sharp and thus thicker the boundary layer can be. The more "opaque" and less transparent the material of the bed is, the correspondingly sharper and less thick the boundary layer can be.

The precise configuration of the boundary layer is heavily dependent on the materials used. The materials must be so selected that, in production, there is a good hold between the two materials used so that the core region cannot detach from the bed upon processing in a processing or milling machine. That can be guaranteed on the one hand by the surface of the bed which is produced first being relatively rough so that the core region which later sets therein adheres well to the bed by virtue of the roughness, being joined to the bed preferably by plastic injection molding. On the other hand—in particular if the situation involves a relatively low level of surface roughness—it can also be provided that a mixture of first material and second material forms the boundary layer. This means that the first material at least partially melts to the second material in the manufacturing procedure and there is thus an intimate join by way of the boundary or mixed layer which is then separate from the bed and from the core regions. That is preferably achieved by the bed first being injection molded. Then the core region is injected on to the bed which is entirely or initially partially hardened. In both variants a relatively sharp enamel-dentine boundary is produced.

The core regions can be of differing shapes and sizes. Preferably, the substantially convex surfaces of the core regions are at least region-wise cylindrical, frustoconical, or parabolic in cross-section. A core region, however, can also be formed from a combination of a plurality of geometries. Thus, a dentine core can also be composed of a plurality of parabolic bodies so that it is possible to produce a reconstruction which is still more natural. It is also possible for the different convex surfaces of the core regions to be of mutually different shapes, in one and the same blank.

To permit production which is as efficient as possible of a plurality of individual constructions or also larger, multi-member tooth prostheses it is preferable that at least five, preferably at least eight, separate core regions are provided in the blank. In that case, it is preferable that those at least five core regions are arranged in a raster shape in the blank. It is particularly preferable, however, that the at least five core regions are arranged at least in a denture shape in the blank. In the ideal case, therefore, at least ten, twelve or fourteen core regions are respectively arranged in denture shape, wherein the core regions are of differing sizes which are approximated to the dentines of a natural denture in respect of shape and size.

For easily gripping the blank in a processing or milling machine it is preferably provided that the blank is of a disk-shape configuration. Depending on the respective design configuration of the processing machine, however, it is also possible to use other shapes like for example cuboidal blanks. To also permit secure gripping or fixing in the machine in positionally accurate relationship an opening, a raised portion, a bore or the like can be provided. Then the precise position of the block (blank) in the processing machine is known in that way. As the position of the cores in the block is also known the position of the cores relative to the machine is also defined and known. The invention is not intended to be limited to the shapes of the core regions which are described and illustrated herein, but any desired shapes can be involved.

A process for the production of a blank according to the invention in a plastic injection molding procedure is also provided. In that case, firstly the bed is injection molded in a first cavity of a mold tool until it is sufficiently hardened. Then, that hardened bed is fitted in a second larger cavity in a mold tool, in which case the second material is injected into the remaining cavity between the hardened bed and the mold tool. After the second material has also hardened the two materials adhere together, that is to say they are joined together by the injection molding operation. The blank can then be suitably milled in a processing or milling machine.

BRIEF DESCRIPTION OF THE DRAWINGS

Further details and advantages of the present invention are described more fully by means of the specific description with reference to the embodiments by way of example set forth hereinafter. In the drawing:

FIGS. 1a-1c are different views of a first embodiment of a blank,

FIGS. 2a-2c are different views of a second embodiment of a blank,

FIG. 5 shows a section through a blank with parabolic core regions, and FIG. 6 shows a section through a blank with differently shaped core regions together with virtually blended-in teeth.

DETAILED DESCRIPTION OF THE INVENTION

Figure 3A:
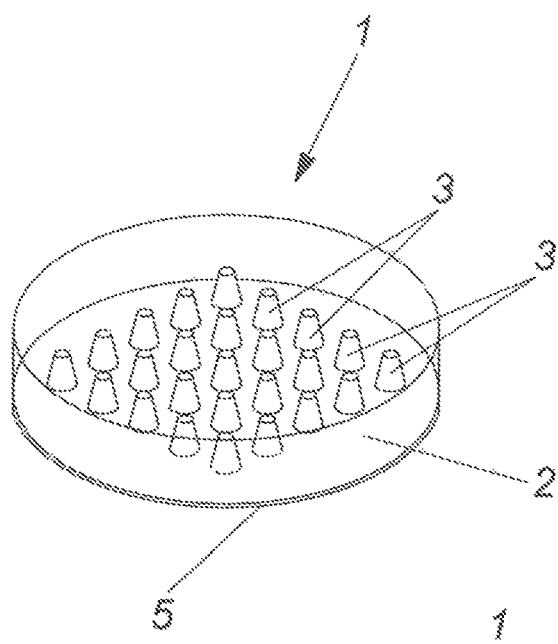
FIGS. 3a-3c show different arrangements of the core regions in a blank.

FIG. 1a is a plan view of a blank 1 in which there are a total of nine core regions 3. Those core regions 3 comprise a second material M2. The core regions 3 are embedded in a bed 2 of a first material M1. Provided at the outer surface R of the blank 1 are recesses 6 by way of which the blank 1 can be gripped in a processing or milling machine (not shown).

The configuration of the core regions 3 and the bed 2 can be clearly seen in the section i-i shown in FIG. 1b, the blank 1 in this case having a plurality of separate core regions 3 with separate surfaces F directed in the direction of the bed 2. In this configuration the surface F is of an entirely convex nature. That surface F together with the surface of the bed 2, that is directed in the direction of the core region 3, forms the boundary layer 4. As a surface, however, the core region has not only the surface F directed in the direction of the bed 2 but also the base surface B that faces away from the bed 2. That base surface B is disposed in the base plane E. All base surfaces B of the core regions 3 are arranged in mutually spaced relationship in the blank 1 and lie in the base plane E. In this first embodiment the base surface B forms the outer surface R of the blank 1.

FIG. 1c is a perspective view illustrating the total of nine core regions 3 with their base surfaces B and surfaces F directed in the direction of the bed 2.

FIG. 2a shows a plan view of a second embodiment of the blank 1. In this case there is additionally provided a basic layer 5 which comprises a material M different from the first material M1, preferably comprising the second material M2.

As can be seen from the section ii-ii shown in FIG. 2b that basic layer 5 is in one piece with the core regions 3. Once again however—as in the first embodiment of FIG. 1b—the base surfaces B facing away from the bed 2 are all disposed on the same base plane E. In addition, disposed on that base plane E are the contact surfaces K of the bed 2, that are directed in the direction of the basic layer 5. Those contact surfaces K are adjoined by the surfaces L of the basic layer 5, that are directed in the direction of the bed 2. This therefore means that the surface L of the basic layer 5, that is directed in the direction of the bed 2, contacts both the base surfaces B of the core regions 3, that are provided separately and in mutually spaced relationship, and also the contact surfaces K of the bed 2. All those surfaces L, B and K lie in the base plane E. As shown in this FIG. 2b therefore the surface of the basic layer 5, that faces away from the bed 2, forms the outer surface R of the blank 1 and not the base surfaces B of the core regions 3, as in the first embodiment.

FIG. 2c with the broken-line view again shows the basic layer 5, in addition viewing practically from above on to the surface of the basic layer L, which contacts the contact surface K of the bed 2 and the base surfaces B of the core regions 3 in the base plane E.

Figure 3B:
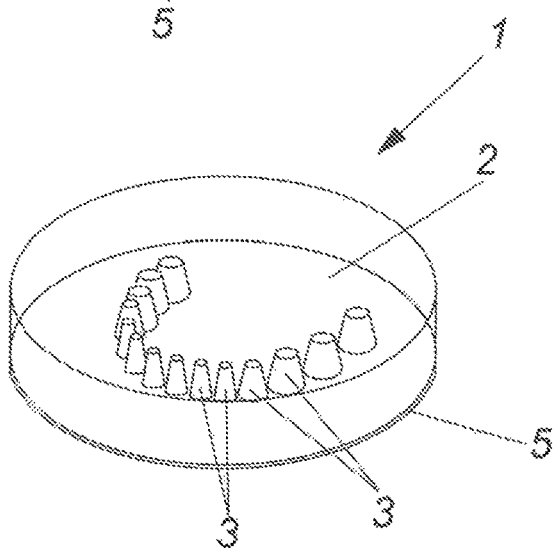
Figure 3C:
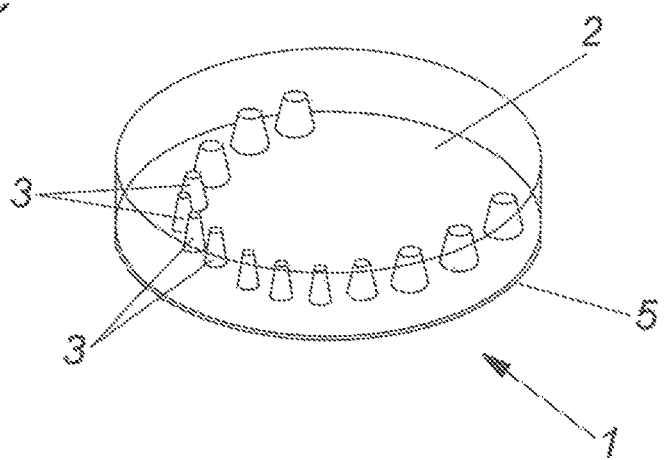

It can be seen from FIGS. 3a through 3c that the core regions 3 can be arranged differently in the blank 1. Those forms can be defined in advance, that is to say prior to production of the blanks 1. Those core regions 3 are surrounded by the bed 2. The individual core regions 3 or the surfaces F thereof can have fine structures as are usual in nature. In FIG. 3a a total of twenty five, substantially identical, core regions are arranged in a raster shape in the blank 1. As shown in FIGS. 3b and 3c respectively fourteen core regions 3 of in part differing sizes are arranged in a denture shape. In FIGS. 3a through 3c all core regions 3 are of a substantially frustoconical configuration. Naturally the core regions 3 can also be of shapes differing therefrom.

Figure 4A:
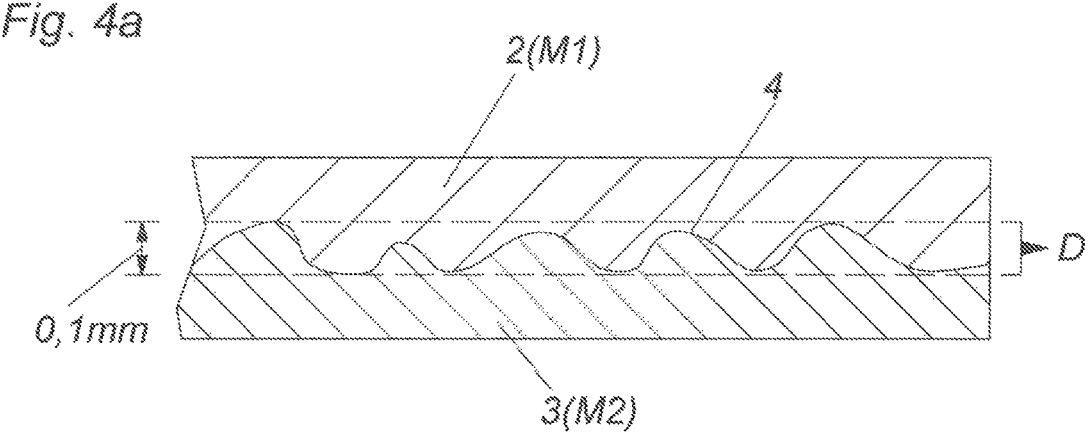
FIGS. 4a and 4b diagrammatically show different configurations of a boundary layer between bed and core region.

FIG. 4a shows a diagrammatic section through a part of the blank 1. More specifically a part in the region of the boundary layer 4 is diagrammatically shown here. In this case the surface roughness of the first material M1 of the bed 2 is relatively great, which is diagrammatically indicated by the relatively high waves. With that relatively great surface roughness (with a surface roughness $R_a$ of between 10 and 15 μm, preferably 12.5 μm) the core region 3 can be intimately joined to the bed 2, without or scarcely without mixing or fusing of the materials M1 and M2. Thus the boundary layer 4 is not an independent layer but is formed by the surfaces of the bed 2 and of the core regions 3, that bear against each other or adhere to each other. For better visualization that boundary layer 4 extends within a region which is of a thickness D of less than 0.1 mm. In many cases the precise thickness D of that region cannot be clearly determined. In principle in that respect it is also possible that, with a polished surface with an Ra of less than 0.01 μm, adequate adhesion is also afforded in the region of the boundary layer 4. That depends in particular on the specific situations of use.

Figure 4B:
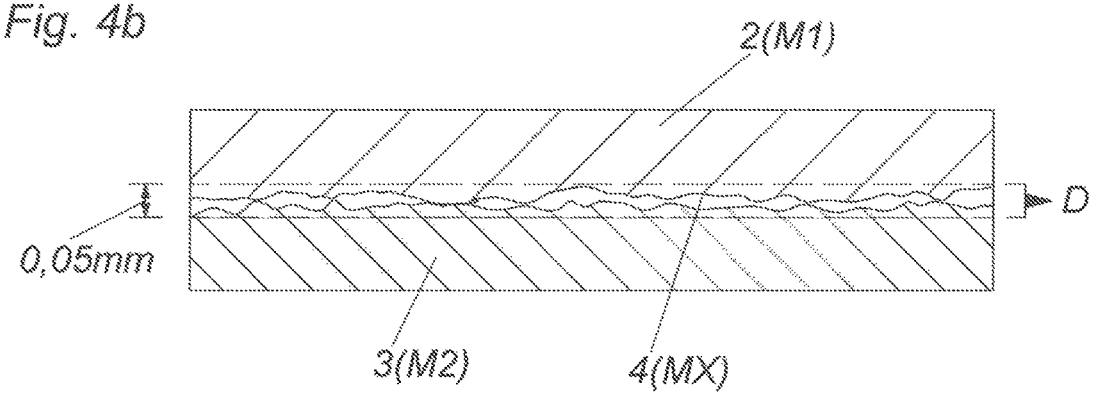

In comparison, as shown in FIG. 4b, a first material M1 with a lesser degree of surface roughness was used for the bed 2. Upon injection of the second material M2 for the core regions the materials M1 and M2 at least partially fuse together whereby the boundary layer 4 is formed from a mixture MX between the first material M1 and the second material M2. That provides an intimate join between the bed 2 and the core regions 3. In this embodiment the boundary layer extends in a region of a thickness D of less than 0.05 mm. As that thickness D also cannot always be precisely determined that space also serves for better visualization.

FIG. 5 shows a section through a blank 1 which illustrates an example of a possible form of the core regions 3. Accordingly the core region 3 is composed of a plurality of parabolic bodies. That shape is similar to a natural structure of a dentine core.

Preferably a multi-component injection molding process is used for manufacture of the blanks 1 (blocks). That affords the best possibility of being able to dispose a plurality of different colors and shapes in a blank 1. Theoretically the production process operates with all thermoplastic materials which in the mutual pairing used have adequate adhesion with each other. In principle however it is also possible to use thermosets. Preferably however thermoplastic materials like for example polymethylmethacrylate (PMMA), polycarbonates (PC), acrylonitrile-butadiene-styrene (ABS), polyethylene (PE), polypropylene (PP), polyetheretherketone (PEEK), polyamide (PA) and so forth. That gives a blank 1 with at least two different constituents (materials M1 and M2) which are of a different color or pigmentation. The core region 3 can also comprise an entirely different chemical material and may have not just a different pigmentation. It would thus also be conceivable to use two-component silicone. Also pressing such a blank 1 from ceramic materials (for example zirconium) is not out of the question. The size of the individual core regions 3 should be substantially approximated to the natural size of the dentines occurring with natural teeth.

Processing of a blank 1 according to the invention can be effected by way of a suitable program or software. In that case a virtual tooth 7 or virtual teeth 7 are placed over the core regions 3 by way of that software. Those virtual teeth 7 can be clearly seen in FIG. 6 where the teeth to be processed are virtually suitably positioned or placed in superposed relationship over differently shaped core regions 3 in the blank 1. As soon as that virtual configuration of the tooth is appropriately positioned the corresponding teeth are milled out of the blank 1 by way of the processing machine (or suitably processed by some other material-removing process). In that case the teeth can be in the form of individual teeth or they can also be milled out in a cohesive arrangement. Depending on which work is respectively involved (individual work or multi-member work) the blank 1 can be of differing configurations. Preferably the blank 1 is adapted to be able to produce a plurality of individual works.

LIST OF REFERENCES 1 blank
2 bed
3 core regions
4 boundary layer
5 basic layer
6 recesses
7 virtual teeth
M1 first material
M2 second material
F surface (direction of bed)
B base surface
E base plane
R outer surface
M material different from M1
L surface of the basic layer
K contact surface
D thickness
MX mixture

The invention claimed is:

1. A blank for the production of a tooth prosthesis, said blank comprising:
   a bed of a first material,
   at least one core region embedded in the bed and having a different color from the bed, the at least one core region comprising a second material and having a surface directed in the direction of the bed, and
   a boundary layer delimiting the bed relative to the surface of the at least one core region directed in the direction of the bed, wherein the boundary layer simulates a dentine boundary between a dental enamel and a dentine,
   wherein the at least one core region comprises at least two separate core regions with separate surfaces directed in the direction of the bed.

2. The blank as set forth in claim 1, wherein each of the at least two core regions has a base surface which adjoins the surface directed in the direction of the bed and which faces away from the bed, wherein each base surface lies in a base plane and wherein the base surfaces of all of the at least two core regions are arranged in mutually spaced relationship in the blank.

3. The blank as set forth in claim 1, wherein the surface of the core region directed in the direction of the bed is substantially convex.

4. The blank as set forth in claim 2, wherein the base surfaces also form an outer surface of the blank.

5. The blank as set forth in claim 2, wherein adjoining the base surfaces of the core regions is a basic layer which is oriented parallel to the base surfaces and which comprises a material different from the first material.

6. The blank as set forth in claim 5, wherein the second material forms the material which is different from the first material, wherein the at least two core regions are in one piece with the basic layer.

7. The blank as set forth in claim 5, wherein the surface of the basic layer directed in the direction of the bed adjoins the base surfaces of the at least two core regions and a contact surface of the bed, the contact surface lying in the base plane.

8. The blank as set forth in claim 1, wherein the blank comprises only the first material and the second material.

9. The blank as set forth in claim 1, wherein the first material and the second material are of mutually different pigmentation and/or are of chemically different nature and/or are of mutually different density.

10. The blank as set forth in claim 1, wherein the boundary layer extends within a range of a thickness of less than 0.3 mm.

11. The blank as set forth in claim 1, wherein a mixture of first material and second material forms the boundary layer.

12. The blank as set forth in claim 1, wherein the second material forming the at least two core regions adheres in the region of the boundary layer to the first material forming the bed.

13. The blank as set forth in claim 1, wherein the surfaces of the at least two core regions are at least region-wise cylindrical, frustoconical, or parabolic in cross-section.

14. The blank as set forth in claim 1, wherein at least five separate core regions are provided in the blank.

15. The blank as set forth in claim 14, wherein the at least five core regions are arranged in raster shape or denture shape in the blank.

16. The blank as set forth in claim 1, wherein the blank has a disk-shaped configuration.

17. A process for the production of the blank as set forth in claim 1, comprising a plastic injection molding process.

18. The blank as set forth in claim 10, wherein the boundary layer extends within a range of a thickness of between 0.001 mm and 0.2 mm.

19. The blank as set forth in claim 14, wherein at least eight separate core regions are provided in the blank.

* * * * *